United States Patent
Park et al.

(10) Patent No.: US 10,004,694 B2
(45) Date of Patent: Jun. 26, 2018

(54) TARGETED POORLY WATER-SOLUBLE DRUG DELIVERY SYSTEM, METHOD OF PREPARING THE SAME, AND PHARMACEUTICAL COMPOSITION INCLUDING THE SAME

(71) Applicant: SAMSUNG LIFE PUBLIC WELFARE FOUNDATION, Seoul (KR)

(72) Inventors: Keunchil Park, Seoul (KR); Jin-Ho Kim, Icheon (KR); Youngwook Kim, Seongnam (KR); Ki Hyun Bae, Bukit Batok (SG)

(73) Assignee: SAMSUNG LIFE PUBLIC WELFARE FOUNDATION, Seoul (KR)

( * ) Notice: Subject to any disclaimer, the term of this patent is extended or adjusted under 35 U.S.C. 154(b) by 0 days. days.

(21) Appl. No.: 14/427,361

(22) PCT Filed: Sep. 12, 2013

(86) PCT No.: PCT/KR2013/008271
§ 371 (c)(1),
(2) Date: Mar. 11, 2015

(87) PCT Pub. No.: WO2014/042450
PCT Pub. Date: Mar. 20, 2014

(65) Prior Publication Data
US 2015/0231087 A1  Aug. 20, 2015

(30) Foreign Application Priority Data
Sep. 12, 2012  (KR) .................. 10-2012-0101040

(51) Int. Cl.
*A61K 9/51* (2006.01)
*A61K 31/337* (2006.01)
(Continued)

(52) U.S. Cl.
CPC .......... *A61K 9/5123* (2013.01); *A61K 9/1272* (2013.01); *A61K 9/5146* (2013.01); *A61K 31/337* (2013.01); *A61K 47/48815* (2013.01)

(58) Field of Classification Search
None
See application file for complete search history.

(56) References Cited

U.S. PATENT DOCUMENTS

| | | |
|---|---|---|
| 6,610,321 B2 | 8/2003 | Huang |
| 7,550,441 B2 | 6/2009 | Farokhzad |
| | (Continued) | |

FOREIGN PATENT DOCUMENTS

| | | |
|---|---|---|
| KR | 10-2010-0085079 | 7/2010 |
| WO | 2012/039685 | 3/2012 |

OTHER PUBLICATIONS

Zhihong Zhang, et al., "HDL-Mimicking Peptide-Lipid Nanoparticles with Improved Tumor Targeting", Small, Feb. 5, 2010, vol. 6, Issue No. 3, pp. 430-437.

Mina Nikanjam, et al., "Synthetic nano-low density lipoprotein as targeted drag delivery vehicle for glioblastoma multiforme", International Journal of Pharmaceutics, Jan. 2, 2007, vol. 328, Issue 1, pp. 86-94.

(Continued)

*Primary Examiner* — Brian Gulledge
(74) *Attorney, Agent, or Firm* — Harness, Dickey & Pierce, P.L.C.

(57) ABSTRACT

Provided are a poorly water-soluble drug delivery system, a method of preparing the same, a method of delivering a poorly water-soluble drug using the same, and a pharmaceutical composition including the same as an effective component, and more particularly, a poorly water-soluble drug delivery system aiming cancer cell specific targeting, which may variously control the kind of a cancer cell targeting material capable of specifically reacting to an antigen overexpressed in a cancer cell, thereby binding to the surface of the poorly water-soluble drug delivery system, and variously control the kind of a poorly water-soluble drug encapsulated therein depending on the kind of cancer and a (Continued)

therapeutic purpose, thereby being effectively applicable to a cancer treatment method.

13 Claims, 10 Drawing Sheets
(10 of 10 Drawing Sheet(s) Filed in Color)

(51) Int. Cl.
  *A61K 47/48* (2006.01)
  *A61K 9/127* (2006.01)

(56) References Cited

U.S. PATENT DOCUMENTS

| | | | | |
|---|---|---|---|---|
| 2004/0247624 | A1* | 12/2004 | Unger | A61K 9/19 424/400 |
| 2008/0182776 | A1* | 7/2008 | Lee et al. | 514/2 |
| 2010/0255108 | A1* | 10/2010 | Lin et al. | 424/491 |
| 2010/0297242 | A1* | 11/2010 | Park | A61K 9/1275 424/489 |
| 2011/0064652 | A1* | 3/2011 | Borlak | A61K 9/007 424/1.11 |
| 2013/0315834 | A1 | 11/2013 | Praveen | |

OTHER PUBLICATIONS

Kenneth K. Ng, et al., "Lipoprotein-Inspired Nanoparticles for Cancer Theranostics", Accounts of Chemical Research, vol. 44, No. 10, May 10, 2011, pp. 1105-1113.
Hyun Ryoung Kim, et al., "Cationic Solid Lipid Nanoparticles Reconstituted from Low Density Lipoprotein Components for Delivery of siRNA", Molecular Pharmaceutics, May 8, 2008, vol. 5, No. 4, pp. 622-631.
The Extended European Search Report, European Patent Office, dated Feb. 24, 2016, European Patent Application No. 13837243.8.
"In vivo evaluation of polymeric micellar paclitaxel formulation: toxicity and efficacy" Journal of Controlled Release 72 (May 2001) 191-202.
European Office Action from corresponding European Patent Application No. 13837243.8 dated Feb. 5, 2018.
Ng, K., et al.; "Lipoprotein-Inspired Nanoparticles for Cancer Theranostics", Accounts of Chemical Research, pp. 1105-1113, vol. 44, No. 10, 2011.
Rege, K., et al.; "Methods in Bioengineering: Nanoscale Bioengineering and Nanomedicine", 2009, pp. 224-225.
Verma, A.., et al.; "Effects of Surface Properties on Nanoparticle-cell Interactions", Wiley InterScience, 2010, 6, No. 1, pp. 12-21.

* cited by examiner

TARGETED POORLY WATER-SOLUBLE DRUG DELIVERY SYSTEM, METHOD OF PREPARING THE SAME, AND PHARMACEUTICAL COMPOSITION INCLUDING THE SAME

TECHNICAL FIELD

The present invention relates to a poorly water-soluble drug delivery system, a method of preparing the same, a method of delivering a poorly water-soluble drug using the same, and a pharmaceutical composition including the same as an effective component.

BACKGROUND ART

Generally, there are three methods for treating cancer: surgical operation, a radiation therapy, and drug treatment. Each method may be used alone, or in combination of two or more methods for treating cancer. Many early stage cancers may be treated by surgical operation, but in case where cancer is much advanced, or metastasis is generated, the treatment is difficult with the surgical operation alone, and a method such as a radiation therapy or drug treatment should be carried out together.

The radiation therapy is to irradiate cancer cells with X-rays or γ-rays, wherein the emitted rays may be used in a surgically inoperable region, or cancer cells having especially good reactivity to radiation, or used before or after surgery. Further, drug treatment is to adopt a method of destructing DNA or enzyme required for the proliferation of cancer cells by administrating a cytotoxic agent orally or by injection. Particularly, the advantage of the drug treatment over the surgical operation or the radiation therapy is to enable a drug to reach any cancer site in the body, and metastatic cancer to be treated, and for this reason, the drug treatment has been widely used as a standard therapy for metastatic cancer treatment. Of course, the drug treatment may not lead the metastatic cancer to be completely cured, but lead symptoms to be relieved, thereby playing an important role in improved quality of life and life extension of patients.

Generally, for drug treatment, chemotherapy using a poorly water-soluble drug such as doxorubicin, cisplatin, taxol, 5-fluorouracil and the like has been widely used so far, but it has a limitation in administration. Since those drugs are poorly water-soluble, even administration of a curable amount may cause severe pain to the patients, and due to excessive side effects, currently the drugs may not be administrated in a large amount. Cause of such side effects is non-selectivity of an anticancer agent, that is, the anticancer agent acts on not only cancer cells, but also normal cells, thereby not killing only cancer cells, but inhibiting growing and causing necrosis of normal cells, and thus, the patients may be seriously pained.

To this end, a delivery system such as micelles and liposomes is prepared to be used to deliver a poorly water-soluble anticancer agent, wherein when the delivery system is prepared, an anticancer agent is added to be contained within the delivery system.

Recently, solid lipid nanoparticles (SLN) which are a delivery system similar to low density lipoprotein (LDL) implementing a natural carrier without causing an immune reaction unlike micelles and liposomes are used as the delivery system for delivering an anticancer agent, wherein the low density lipoprotein (LDL) is basically involved in lipid and protein mobilization, specifically cholesterol delivery to external tissues of a liver in entire systemic circulation. In practice, a non-hydrophilic drug such as cyclosporine A and amphotericin B lipid complex salt (ABLC) was effectively delivered by binding the drug to LDL in pre-clinical or clinical treatment.

However, since a method of separating natural low density lipoprotein (LDL) from blood is too complicated and time-consuming, solid lipid nanoparticles which are a biomimetic model of the low density lipoprotein (LDL) have been developed from cholesteryl ester and phospholipid, instead of not containing apolipoprotein.

However, a delivery system which is the existing solid lipid nanoparticles, is absorbed in a phagocyte present in a liver, or released in a short time by a kidney, thereby not sufficiently delivering an anticancer agent encapsulated therein to a cancer tissue, and thus, it is problematic due to a limitation in an effective anticancer treatment.

DISCLOSURE OF INVENTION

Technical Problem

In order to solve the problems of the prior art as described above, an object of the present invention is to provide low density lipoprotein (LDL)-like nanoparticles prepared by mimicking constituents of low density lipoprotein in nature to reconstruct surface modification, and binding a targeting antibody to the surface; a composite including the LDL-like nanoparticles and a poorly water-soluble drug; a targeting poorly water-soluble drug delivery system having improved apoptosis efficiency and stability and reduced toxicity, using the composite; and a method of manufacturing them.

Another object of the present invention is to provide a composite including LDL-like nanoparticles and a poorly water-soluble drug, not causing an immune reaction, unlike micelles and liposomes; a targeting poorly water-soluble drug delivery system including a poorly water-soluble drug, having improved apoptosis efficiency and stability and reduced toxicity, using the composite; and a method of manufacturing them.

Another object of the present invention is to provide a method of delivering a targeting poorly water-soluble drug, having improved apoptosis efficiency and stability and reduced toxicity, using the LDL-like nanoparticles.

Another object of the present invention is to provide a pharmaceutical composition containing the poorly water-soluble drug delivery system as an effective component.

However, objects of the present invention are not limited to the objects described above, and other objects that are not described above may be clearly understood by those skilled in the art from the following description.

BRIEF DESCRIPTION OF DRAWINGS

The file of this patent contains at least one drawing executed in color. Copies of this patent with color drawing(s) will be provided by the Patent and Trademark Office upon request and payment of the necessary fee.

of a poorly water-soluble drug delivery system (In this drawing, an arrow represents the time when a drug is injected).

Figure 4:
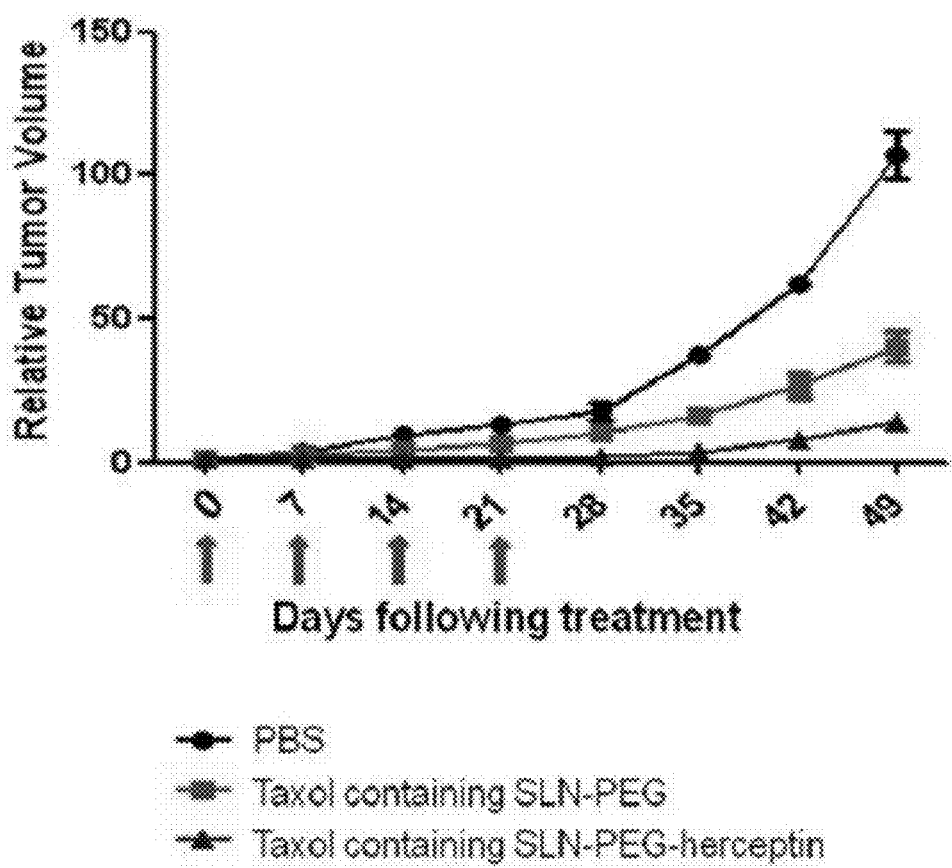

FIG. 4 is a graph of volumes of cancer tissues over time measured according to the method of Example 3-4, in order to check the therapeutic effect against cancer (breast cancer) of a poorly water-soluble drug delivery system (In this drawing, an arrow represents the time when a drug is injected).

Figure 5:
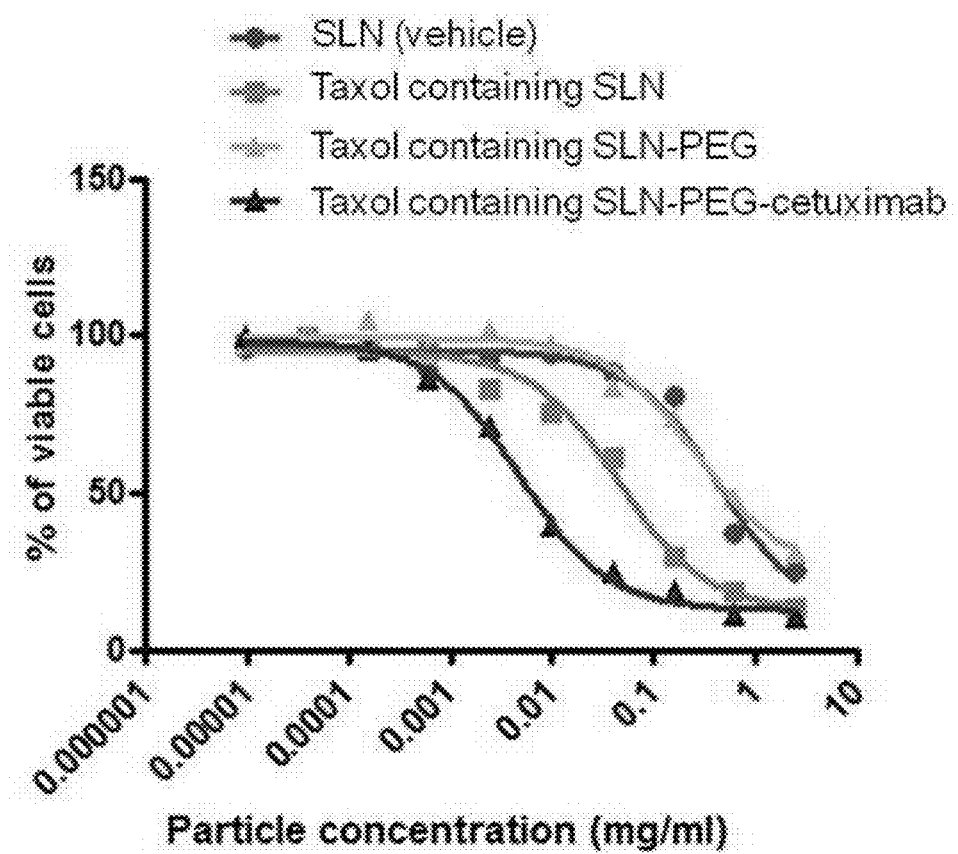

FIG. 5 represents a MTT analysis according to Example 4-2 in a NCI-H1975 cell line.

Figure 6:
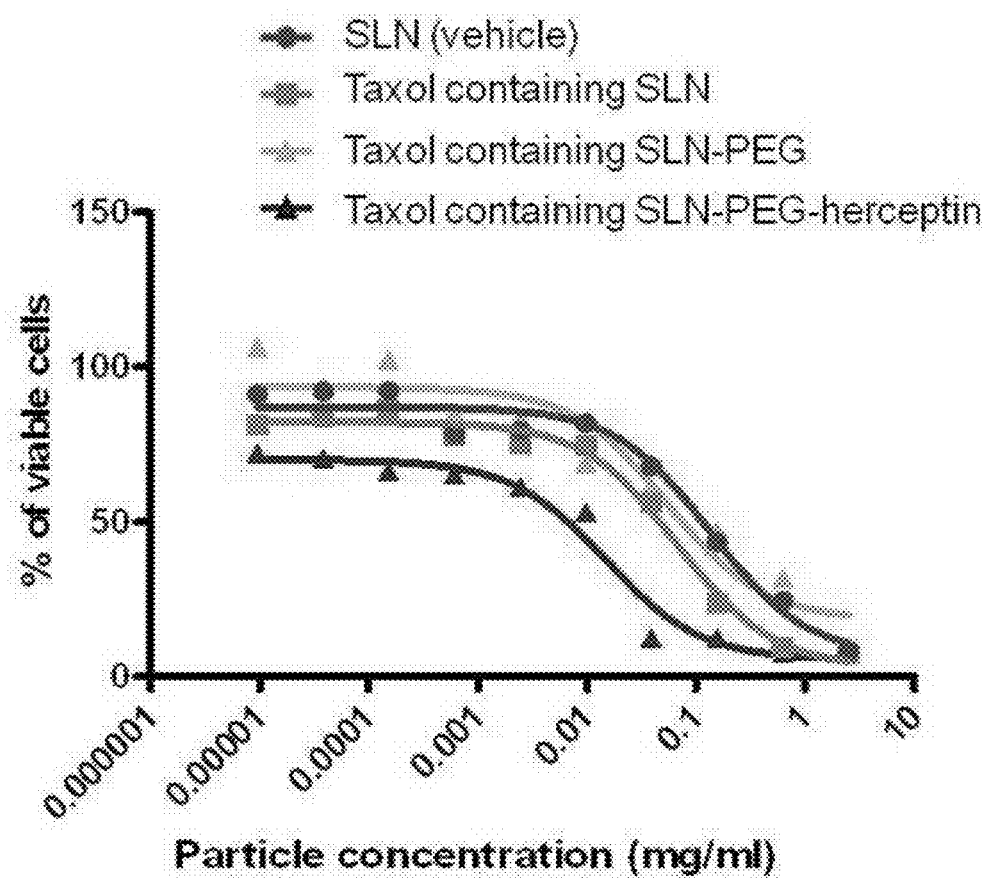

FIG. 6 represents a MTT analysis according to Example 4-3 in a SK-BR-3 cell line.

Figure 7:
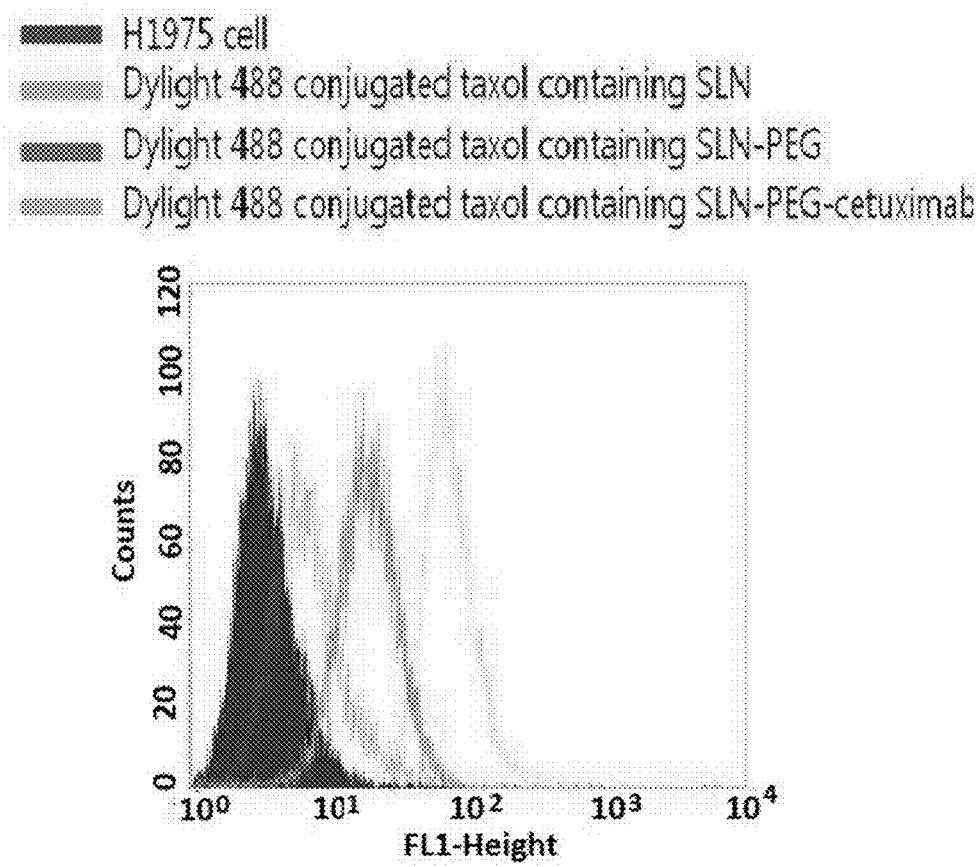

FIG. 7 represents evaluation of transfer efficiency (FACS analysis) in a NCI-H1975 cell line according to Example 5-5.

Figure 8:
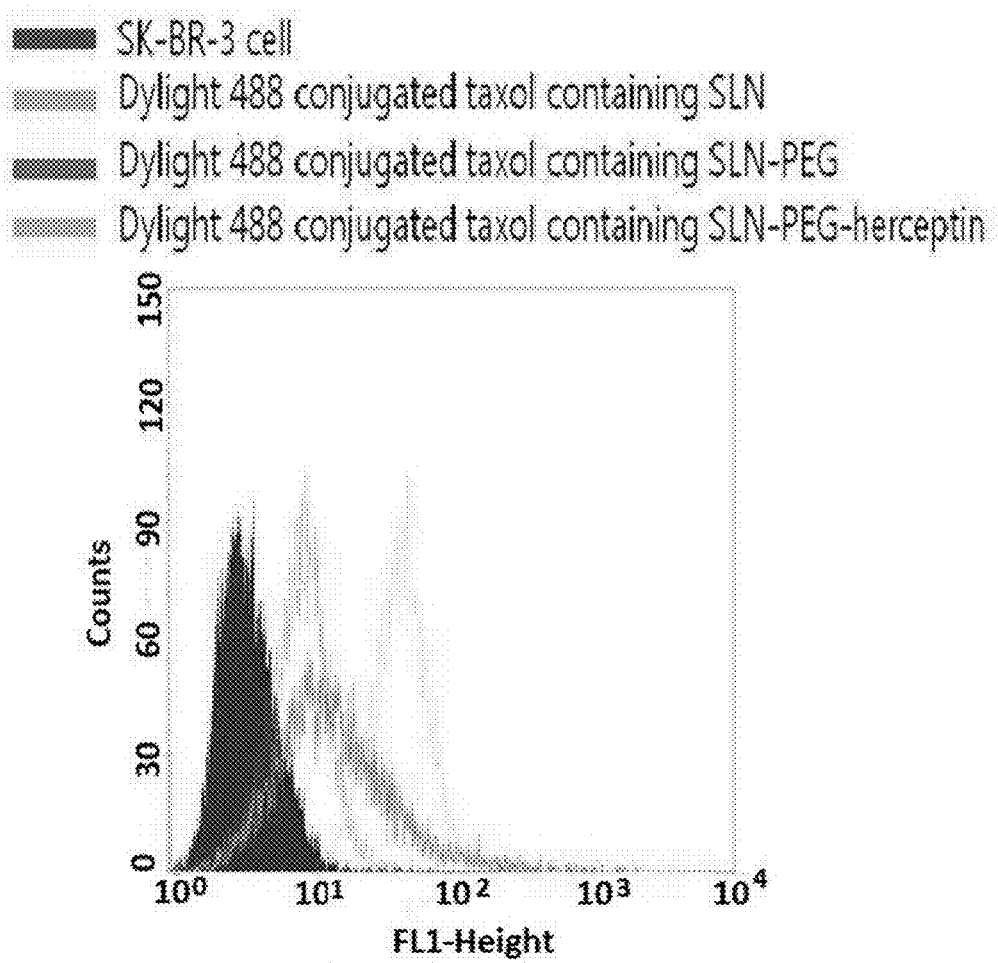

FIG. 8 represents evaluation of transfer efficiency (FACS analysis) in a SK-BR-3 cell line according to Example 5-6.

Figure 9:
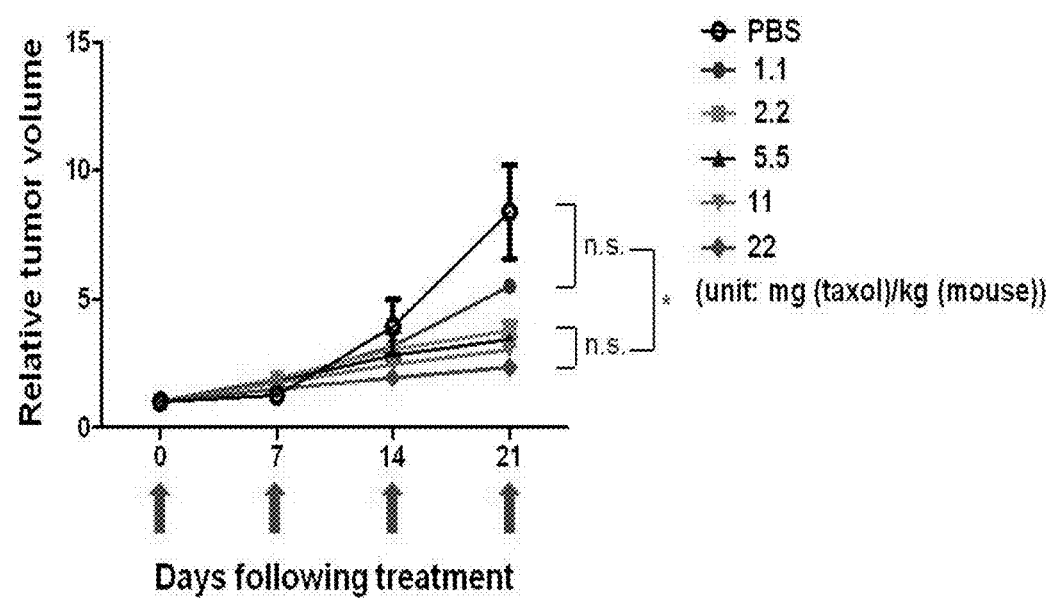

FIG. 9 is a graph of volumes of cancer tissues depending on the concentration of injected taxol containing SLN-PEG (derivative)-cetuximab (In this drawing, an arrow represents the time when a drug is injected).

Figure 10:
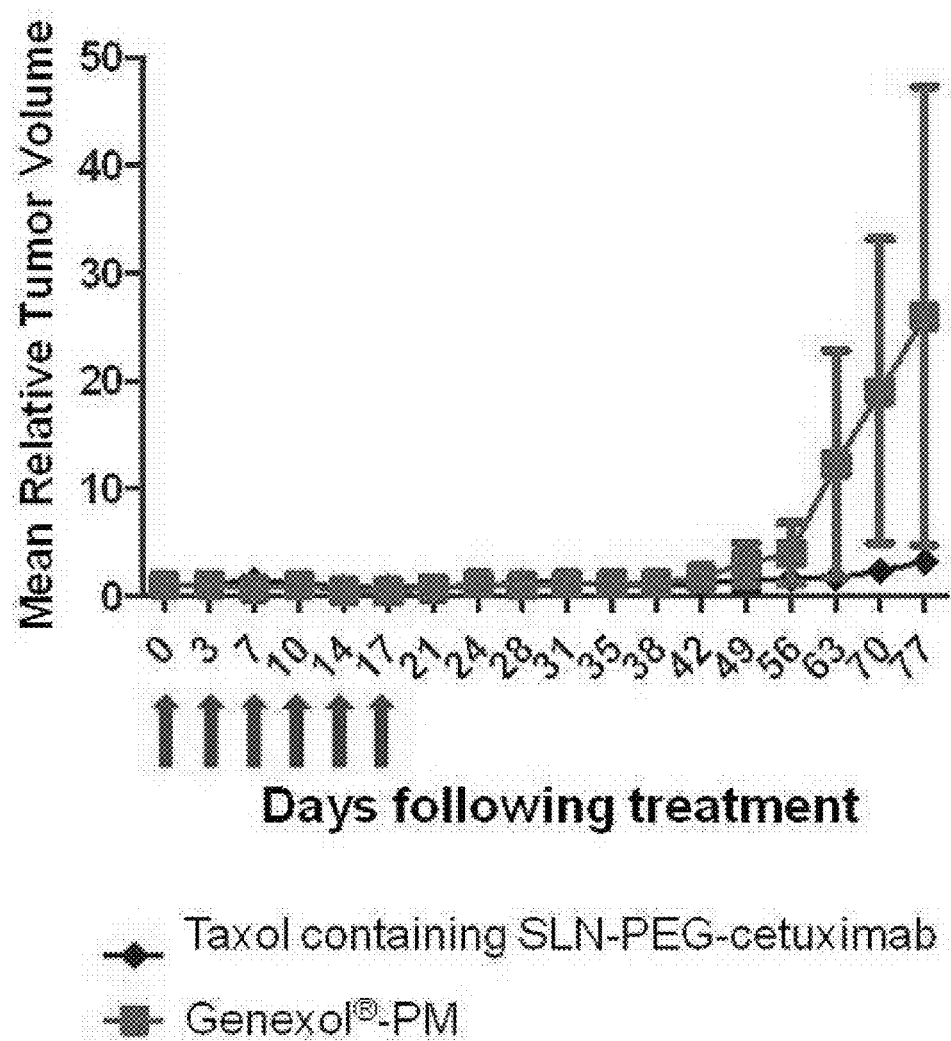

FIG. 10 is a graph of anticancer effect comparison of taxol containing SLN-PEG (derivative)-cetuximab and Genexol®-PM (In this drawing, an arrow represents the time when a drug is injected).

(PEG in FIGS. 1 and 3 to 10 refers to a PEG derivative.)

Technical Solution

As means for solving problems as above, low density lipoprotein (LDL)-like nanoparticles prepared by mimicking constituents of low density lipoprotein in nature to reconstruct surface modification, and binding a targeting antibody to the surface; a composite including the LDL-like nanoparticles and a poorly water-soluble drug; a targeting poorly water-soluble drug delivery system including a poorly water-soluble drug, having improved apoptosis efficiency and stability and reduced toxicity, using the composite; and a method of manufacturing them, are provided.

A low density lipoprotein in nature includes a surface lipid part consisting of two lipid phases, that is, phospholipid and apolipoprotein, and a core lipid part consisting of cholesteryl ester and triglyceride, and the composition is as described in Table 1 below:

TABLE 1

| Classification | Components | Content ratio (W/W) |
| --- | --- | --- |
| Surface lipid part | Phospholipid | 22 |
| | Cholesterol | 10 |
| | Apolipoprotein B-100 | 20 |
| Core lipid part | Cholesteryl ester | 45 |
| | Triglyceride | 3 |

Phospholipid and apolipoprotein of a surface lipid part emulsifies a nonpolar lipid consisting of cholesteryl ester and triglyceride of a core lipid part to provide surface stabilization, thereby forming stable biological microemulsion.

However, a method of separating low density lipoprotein (LDL) in nature from blood is too complicated and time consuming, and thus, a delivery system as a LDL mimic model has been developed from cholesteryl ester and phospholipid, instead of containing apolipoprotein.

Since the delivery system mimicking the structure and composition of a natural carrier does not cause an immune reaction, unlike micelles and liposomes, it may be developed into an in vivo drug delivery system.

The present inventors have found out that poorly water-soluble anticancer agent is delivered to a cancer cell with high efficiency, by binding a polymer for increasing in vivo residence time of a delivery system to a surface of the delivery system, and binding a targeting antibody recognizing an antigen especially present only in a cancer cell to a polymer attached to the surface of the delivery system, with a method of selectively targeting a delivery system including the LDL-like solid nanoparticles and a poorly water-soluble drug, for example, a poorly water-soluble anticancer agent encapsulated in the inner core lipid part at cancer cells.

The present invention provides a LDL-like solid nanoparticle including a core lipid part containing cholesteryl ester and triglyceride; a surface lipid part containing phospholipid, cholesterol and cationic lipid; a polymer linker connected to the surface lipid part; and a targeting material connected to the polymer linker.

Further, the present invention provides a targeting drug delivery system including a composite including a poorly water-soluble drug encapsulated in a core lipid part of the LDL-like solid nanoparticle.

In order to deliver a drug to a target effectively, an ability of a drug delivery system to remain in blood for substantial period of time without being removed is essential. Therefore, a size and surface properties of an administered drug delivery system are important.

The surface charge of the LDL-like solid nanoparticles and the poorly water-soluble drug delivery system may be −10 to 10 mV, and in order to deliver the drug to a targeted tissue more effectively, it may be preferably −3 to 3 mV.

In case where the surface of a drug delivery system is ionic or hydrophobic, the drug delivery system is caught by a macrophage positioned in a reticulo-endothelial system within a liver or a spleen to be removed, and more specifically, in case where the surface of a drug delivery system is ionic or hydrophobic, the drug delivery system may be adsorbed (opsonized) in plasma proteins such as fibronectin, a complements and IgG by electrostatic attraction, thereby being recognized by a macrophage in a reticulo-endothelial system, and consequently, the drug delivery system is removed. Therefore, in order to escape from the phagocytosis of the macrophage, it is preferred to make the surface of the poorly water-soluble drug delivery system neutral or close to neutral.

The size of the poorly water-soluble drug delivery system may be 30 to 300 nm, and in order to deliver the drug to a targeted tumor tissue more effectively, it is preferably 150 to 250 nm. If the size of the drug delivery system is too small, the drug delivery system may pass through normal blood to deliver the drug to a normal tissue as well as a tumor tissue, and also a drug payload encapsulated within the drug delivery system may be insufficient. If the size is too large, the drug delivery system may be caught by a macrophage positioned in a reticulo-endothelial system in a liver or a spleen during body circulation to be removed.

As an exemplary embodiment of the present invention, a composite including the LDL-like nanoparticles and a poorly water-soluble drug may contain 20 to 60% by weight of cholesteryl ester; 0.1 to 10% by weight of triglyceride; 5 to 30% by weight of phospholipid; 3 to 20% by weight of cholesterol; 10 to 50% by weight of cationic lipid; and 10 to 20% by weight of a poorly water-soluble drug, and considering the encapsulation efficiency of the poorly water-soluble, preferably, contain 24 to 28% by weight of cholesteryl ester; 1 to 3% by weight of triglyceride; 14 to 18% by weight of phospholipid; 3 to 7% by weight of cholesterol; 30 to 35% by weight of cationic lipid; and 14 to 18% by weight of a poorly water-soluble drug, based on total weight of the composite.

The cholesteryl ester applicable to the present invention may be an ester compound of cholesterol and an unsaturated aliphatic acid having 10 to 24 carbon atoms.

The triglyceride applicable to the present invention may be one or more selected from the group consisting of triacetin, tributyrin, tricaproin, tricaprylin, tricaprin and triolein.

The phospholipid applicable to the present invention may be one or more selected from the group consisting of dioleoylphosphatidylethanolamine (DOPE), palmitoyloleoylphosphatidylcholine (POPC), egg phosphatidylcholine (EPC), distearoylphosphatidylcholine (DSPC), dioleoylphosphatidylcholine (DOPC), dipalmitoylphosphatidylcholine (DPPC), dioleoylphosphatidylglycerol (DOPG) and dipalmitoylphosphatidylglycerol (DPPG).

The cationic lipid applicable to the present invention may be one or more selected from the group consisting of 3β-[N—(N',N',N'-trimethylaminoethane)carbamoyl]cholesterol (TC-cholesterol), 3β[N—(N',N'-dimethylaminoethane)carbamoyl]cholesterol (DC-cholesterol), 3β[N—(N'-monomethylaminoethane)carbamoyl]cholesterol (MC-cholesterol), 3β-[N -(aminoethane)carbamoyl]cholesterol (AC-cholesterol), N—(N'-aminoethane)carbamoylpropanoic tocopherol (AC-tocopherol), N—(N'-methylaminoethane)carbamoylpropanoic tocopherol (MC-tocopherol), N,N-dioleyl-N,N-dimethylammonium chloride (DODAC), N,N-distearyl-N,N-dimethylammonium bromide (DDAB), N-(1-(2,3-dioleoyloxy)propyl-N,N,N-trimethylammonium chloride (DOTAP), N,N-dimethyl-(2,3-dioleoyloxy)propylamine (DODMA), N-(1-(2,3-dioleoyloxy)propyl)-N,N,N-trimethylammonium chloride (DOTMA), 1,2-dioleoyl-3-dimethylammonium-propane (DODAP), 1,2-dioleoylcarbamyl-3-dimethylammonium-propane (DOCDAP), 1,2-dilineoyl-3-dimethylammonium-propane (DLINDAP), dioleoyloxy-N-[2-(sperminecarboxamido)ethyl]-N,N-dimethyl-1-propanaminium trifluoro-acetate (DOSPA), dioctadecyl-amidoglycylspermine (DOGS), 1,2-dimyristyloxypropyl-3-dimethyl-hydroxyethylammonium bromide (DMRIE), 3-dimethylamino-2-(cholest-5-en-3-β-oxybutan-4-oxy)-1-(cis,cis-9,12-octadecadieneoxy) propane (CLinDMA), 2-[5'-(cholest-5-en-3β-oxy)-3'-oxapentoxy)-3-dimethyl-1-(cis,cis-9',12'-octadecadieneoxy) propane (CpLinDMA), N,N-dimethyl-3,4-dioleoyloxybenzylamine (DMOBA), 1,2-N,N'-dioleylcarbamyl-3-dimethylaminopropane (DOcarbDAP), 1,2-diacyl-3-trimethylammonium-propane (TAP), and 1,2-diacyl-3-dimethylammonium-propane(DAP).

The polymer linker applicable to the present invention may be one or more selected from the group consisting of polyethylene glycol (PEG), polylactic acid (PLA), polyglycolic acid (PGA), polyester, polyorthoester, polyanhydride, peptide, polyhydroxyalkanoate (PHA), polycaprolactone (PCL), polyalkyl carbonate, albumin, gelatin, collagen, fibrin, alginic acid, chitin, chitosan, dextran, hyaluronic acid, starch and their derivatives, wherein the derivative refers to a compound in which a hydrogen atom or a certain atomic group of the polymer linker is substituted by another atom or atomic group.

The polymer linker may contain may contain a functional group capable of being bound to a surface lipid part of a nanoparticle on one end, and a functional group capable of being bound to a targeting antibody on the other end. As a specific example, the polymer linker may have —NHS (succinimide group), —CHO (aldehyde group) or —COOH (carboxyl group) capable of being bound to cationic amine (—NH$_2$) present on a surface lipid part of a nanoparticle on one end, and a maleimide group, —COOH (carboxyl group) or —SH (thiol group) capable of being bound to —SH (thiol group) present in a targeting antibody on the other end.

Since PEG which is a hydrophilic polymer, has an ability to inhibit adsorption of plasma proteins, it serves to increase in vivo circulation time of the drug delivery system, and the polymer linker may be PEG or a derivative thereof. If the PEG or a derivative thereof has a molecular weight less than 500, the PEG derivative may be oxidized to a toxic compound by in vivo alcohol dehydrogenase, and if it has a molecular weight more than 50,000, there may be problems in manufacture. Therefore, the molecular weight may be 500 to 50,000, preferably 2,000 to 20,000. A specific example of the PEG derivative may be a compound of following Chemical Formula 1:

[Chemical Formula 1]

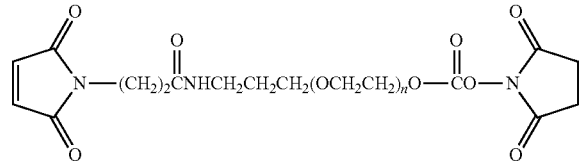

wherein n is an integer of 4 to 1,130, preferably 38 to 447.

Specifically, a polyethylene glycol derivative is bound to a nanoparticle surface by an amide bond formed between cationic amine (—NH$_2$) present on the surface lipid part of the nanoparticle and —NHS present on one end of the polymer linker.

The targeting antibody is bound to a nanoparticle surface by a chemical bond formed between a maleimide group, —COOH (carboxyl group) or —SH (thiol group) present on the other end, that is, the outer end of the polymer linker, and —SH (thiol group) present in a targeting antibody.

In an exemplary embodiment of the present invention, the targeting material may be one or more selected from the group consisting of bevacizumab, erlotinib, Gefitinib, imatinib mesylate, cetuximab, rituximab, trastuzumab, folate and RGD.

In an exemplary embodiment of the present invention, the poorly water-soluble drug may be one or more selected from the group consisting of a poorly water-soluble anticancer agent, an antiviral agent, a steroidal anti-inflammatory drug, an antibiotic, an antifungal, vitamins, prostacyclin, an antimetabolic agent, a mitotic, an adrenaline antagonist, an anticonvulsant, an antianxiety agent, a tranquilizer, an antidepressant, an anesthetic agent, an analgesic agent, an anabolic steroid agent, an immunosuppressant and an immune stimulant, and the poorly water-soluble anticancer agent may be one or more selected from the group consisting of taxol, idarubicin, mitoxantrone, paclitaxel, docetaxel, methotrexate, trimetrexate, thioguanine, mercaptopurine, cladribine, amrubicin, octreotide, gosereline, leuprolide, flutamide, casodex, doxorubicin, 5-fluorouracil, fludarabine, cytarabine, mitomycin-C, styrene maleic acid neocarzinostatin (SMANCS), cisplatin, carboplatin, oxaliplatin, carmustine (BCNU), dacabazine, etoposide, daunomycin, dactinomycin, vinca alkaloid, bleomycin, cyclophosphamide, ifosfamide, gemcitabine, pemetrexed, camptothecin, irinotecan, topotecan, chlorambucil and melphalan.

Further, the present invention provides a method of preparing a composite of nanoparticles having a drug encapsulated in a core lipid part, including dissolving cholesteryl ester, triglyceride, phospholipid, cholesterol, cationic lipid and a poorly water-soluble drug in an organic solvent, and then adding water thereto, thereby preparing a composite of nanoparticles enclosing a poorly water-soluble drug; binding a polymer linker to a surface of the composite by an amide bond; and binding a targeting antibody to the polymer linker.

The organic solvent may be a hydrophobic and/or hydrophilic solvent; the hydrophobic solvent includes chloroform, cyclohexane, and the like, and the hydrophilic solvent includes ethanol, methanol, and the like. The hydrophilic and hydrophobic solvents may be used alone, or in combination in a certain ratio, but are not limited thereto.

The organic solvent may be used to dissolve lipid components used for synthesizing nanoparticles. Thereafter, when water is added to make nanoparticles (O/W emulsion) representing a cationic property on a surface by self-assembly of lipid components, the used organic solvent is removed.

More specifically, the condition for removing the organic solvent is characterized by evaporating the organic solvent at a temperature higher than the melting point of cholesteryl ester, in addition to evaporating the organic solvent at a temperature higher than the boiling point of the organic solvent. Since cholesteryl ester undergoes phase change from solid to liquid at a temperature higher than the melting point, such characteristic is to allow the organic solvent present within a nanoparticle to diffuse well into the outside of the nanoparticle, so that the removal of the organic solvent within the nanoparticle may be facilitated, thereby making the core part of the nanoparticle stable. For example, since cholesterol oleate having a melting point of 52° C. is liquid at a temperature higher than a melting point, when the organic solvent is removed at a temperature of 52° C. or more in the manufacture of nanoparticles, the organic solvent present in the liquid core part is removed to the outside of the nanoparticles and then evaporated, and at the same time, through a process where the core part of the nanoparticles is reassembled once again using the flowability of the liquid cholesterol oleate, stable nanoparticles are formed.

Therefore, the organic solvent should have a boiling point higher than the melting point of cholesteryl ester and lower than the boiling point of water. For example, considering that the melting point of cholesterol oleate is 52° C., it is preferred that the organic solvent has a boiling point of 52° C. to 80° C.

If cationic amine present on a surface lipid part of the nanoparticle is bound to a polyethylene glycol derivative, a surface charge of the nanoparticle is neutralized, there is less possibility of being captured by a macrophage, and thus, in vivo circulation time is increased, so that a possibility of delivering the drug to a cancer tissue may be increased.

A mole ratio between a cationic amine group ($-NH_2$) contained in cationic lipid of the surface lipid part and a functional group contained the polymer linker may be 1:1 to 1:5, preferably 1:1 to 3.5, and as a specific example, 1:2, 1:1.5, or 1:3. As a specific example, reactants are added to the reaction so that the mole ratio of the cationic amine group to a —NHS functional group of PEG is in the above range. As the cationic amine group is bound to the functional group of the polymer linker as many as possible, a surface charge of the nanoparticle may be close to 0. If the polymer linker has one functional group capable of being bound to the amine group in one molecule, the mole ratio of the functional group contained in the polymer linker may be the mole ratio of the polymer linker.

The targeting antibody is bound to the nanoparticle by a chemical bond formed between a functional group present in the outer end of the polymer linker and a thiol group of the targeting antibody. Specifically, the targeting antibody is bound to the nanoparticle surface by a chemical bond formed between a maleimide group present in the other end of the polyethylene glycol derivative of the above Chemical Formula 1 and a thiol group present in a targeting antibody. A reaction mole ratio of a functional group capable of being bound of the polymer linker to a functional group of the targeting material may be 1:1 to 1:10, preferably 1:2 to 1:7, for example, 1:3, 1:3.5, 1:4, 1:4.5, 1:5, 1:5.5, 1:6, or 1:6.5. In the mole ratio, as the targeting material is bound to the polyethylene glycol derivative as much as possible, a surface charge may be close to 0. The surface charge has a technical advantage capable of actively adjusting the number of molecules of the targeting antibody bound to the maleimide group present in the outer end of the polyethylene glycol derivative for binding. As a specific example, if the functional group capable of being bound of the polymer linker is contained in one within one molecule, and the functional group of the targeting material is contained in one within one molecule, the mole ratio may be the mole ratio between the polymer linker and the targeting material, added respectively.

In case of the targeting antibody without a thiol group capable of being bound to an end functional group of the polymer linker, it may be bound to the polymer linker by substituting the amine group of the antibody with the thiol group, and thus, by utilizing this, it is possible to introduce various targeting material to a poorly water-soluble drug delivery system. Thus, the poorly water-soluble drug delivery system developed by the present invention may have a technical advantage of controlling the targeting material bound to the polymer linker actively and variously depending on an antigen overexpressed in a cancer cell.

Further, the present invention provides a pharmaceutical composition containing the poorly water-soluble drug delivery system as an effective component. Specifically, the pharmaceutical composition may contain the poorly water-soluble drug delivery system in a range of 20 to 200 mg/kg.

The pharmaceutical composition may be administered to a mammal including a human being in a variety of routes including parenteral administration. The parenteral administration may be applied intravenously, subcutaneously, abdominally or topically, and since the only route to deliver a drug to a cancer cell tissue is through a blood vessel, the most preferred example includes using intravenous administration (I.V.). A dosage varies with state and weight of a patient, disease severity, a drug form, an administration route and time, but may be appropriately selected by a person skilled in the art.

If the pharmaceutical composition according to the present invention is formulated, generally used diluent or excipient such as filler, extender, binder, wetting agent, disintegrant and surfactant are used in the preparation.

The preparation for parenteral administration may include a sterile aqueous solution, a non-aqueous solvent, a suspension solvent, emulsion, a freeze-dried preparation, a suppository and the like.

As a non-aqueous solvent and a suspension solvent, propylene glycol, polyethylene glycol, a vegetable oil such as an olive oil, injectable ester such as ethyloleate, and the like may be used. As a base of the suppository, witepsol, macrogol, tween 61, cacao butter, laurinum, glycerol, gelatine, and the like may be used.

The pharmaceutical composition according to the present invention may be administered in a pharmaceutically effective amount. In the present invention, "pharmaceutically effective amount" refers to an amount sufficient to treat a disease in a reasonable benefit/risk ratio applicable to medical treatment, and an effective dose level may be determined by factors including the kind and severity of the disease of a patient, an activity of a drug, sensitivity to a drug, administration time, administration route and releasing rate, treatment period and a simultaneously used drug, and other factors well known in the medical field. The pharmaceutical composition of the present invention may be administered as an individual therapeutic agent, or in combination with other therapeutic agents, sequentially or simultaneously with the traditional therapeutic agent, and in a single or multiple. It is important to administer an amount for obtaining a maximum effect with a minimum amount without any side effect, considering all of the above elements, and this may be easily determined by a person skilled in the art.

Specifically, the effective amount of the compound according to that present invention may be varied with the age, gender and weight of a patient, and generally the poorly water-soluble drug may be administered in 0.1 to 100 mg, preferably 0.5 to 10 mg per 1 kg of body weight, every day or every other day, or by dividing into 1 to 3 times a day. However, the amount may be increased or decreased depending on the administration route, severity of obesity, gender, weight, age, and the like, and thus, the administration amount in no way limits the scope of the present invention.

Advantageous Effects

In case where the poorly water-soluble drug delivery system of the present invention is injected in vivo, the probability of delivering the poorly water-soluble drug delivery system to a cancer cell was increased due to the polymer and targeting material bound to the surface of the poorly water-soluble drug delivery system, and since the poorly water-soluble drug was encapsulated in the poorly water-soluble drug delivery system stably and in a high efficiency, the drug delivered to a cancer cell by the poorly water-soluble drug delivery system showed excellent cancer cell apoptosis. Further, the kind of the cancer cell targeting material capable of specifically reacting to an antigen overexpressed in a cancer cell is variously controlled, so that the cancer cell targeting material may be bound to the surface of the poorly water-soluble drug delivery system, and the kind of the poorly water-soluble drug encapsulated therein may be variously controlled depending on the kind of cancer and a therapeutic purpose.

Best Mode For Carrying Out The Invention

Hereinafter, the present invention will be described in detail, by following Examples. However, those Examples are only for illustrating the present invention, and do not limit the scope of the present invention.

EXAMPLES

Example 1

Preparation of Poorly Water-soluble Drug Delivery System 1-1: Preparation of Solid Lipid Nanoparticle Enclosing Taxol (Taxol Containing SLN)

As shown in following Table 2, 8.4 mg (26.8% by weight) of cholesteryl oleate, 0.5 mg (1.6% by weight) of triolein, 5.2 mg (16.6% by weight) of DOPE, 1.8 mg (5.7% by weight) of cholesterol, 10.5 mg (33.4% by weight) of DC-cholesterol, and 5 mg (15.9% by weight) of taxol were dissolved in 2 mL of chloroform:methanol (2:1) solution in a glass bottle. 10 mL of distilled water was added to the glass bottle, and mixed for 1 minute by vortexing, thereafter, the solution was sonicated by Branson sonifier 450 (20 kHz, duty cycle=40, output control=3.5) for 3 minutes. The solution was transferred to a rotary evaporator, and chloroform:methanol (2:1, v/v) solution as a solvent was removed at a temperature of 60° C. or more being a melting point of cholesteryl oleate. Purification was carried out in distilled water for one night using a dialysis membrane of molecular weight of cut-off (MWCO) of 5000, and a solid lipid nanoparticle solution enclosing the purified poorly water-soluble drug (taxol) was stored at 4° C. to prepare solid lipid nanoparticles enclosing poorly water-soluble drug (taxol) (taxol containing SLN).

TABLE 2

| Classification | Components | Content (mg) | Content ratio (%) |
|---|---|---|---|
| Surface lipid part | DOPE | 5.2 | 16.6 |
| | Cholesterol | 1.8 | 5.7 |
| | DC-chol | 10.5 | 33.4 |
| Core lipid part | Cholesteryl oleate | 8.4 | 26.8 |
| | Triolein | 0.5 | 1.6 |
| Drug (core) | Taxol | 5 | 15.9 |

1-2: Physical and Chemical Properties of Solid Lipid Nanoparticle Enclosing Poorly Water-soluble Drug (Taxol)

The average size and zeta-potential of the solid lipid nanoparticle enclosing the poorly water-soluble drug (taxol) prepared in Example 1-1 were measured by a laser light scattering method, using a dynamic light scattering machine (DSL) (Zeta-Plus, Brookhaven Instruments, NY) having a He—Ne laser of wavelength of 632 nm and a detection angle of 90° mounted thereon. The size was measured three times when the concentration of solid lipid nanoparticles (as prepared in Example 1-1) enclosing the poorly water-soluble drug (taxol) dispersed in distilled water at 25° C. was 5 mg/ml, and in order to evaluate the content and the encapsulation rate of the drug contained in the solid lipid nanoparticles enclosing the poorly water-soluble drug (taxol), high performance liquid chromatography (HPLC) was used.

A solid lipid nanoparticle solution enclosing the poorly water-soluble drug (taxol) was freeze-dried to remove distilled water. The solid lipid nanoparticles enclosing the freeze-dried poorly water-soluble drug (taxol) were dispersed in 20 ml of methanol to be completely dissolved, and then the poorly water-soluble drug was extracted through a filter (Millex SR 0.45 um filter unit), thereafter, the amount of the poorly water-soluble drug was analyzed using high performance liquid chromatography, and the results are described in following Table 3.

Herein, the amount of poorly water-soluble drug was subjected to quantitative analysis by comparing with a calibration curve depending on the concentration of the drug, and the amount (%, w/w) and the encapsulation rate (%) of the encapsulated poorly water-soluble drug were analyzed as following Equation 1:

$$\text{Enclosure rate (\%)} = \frac{\text{Measured amount of drug (mg)}}{\text{Amount of drug used for synthesis (mg)}} \times 100 \quad \text{[Equation 1]}$$

$$\text{Drug content (\%, w/w)} = \frac{\text{Measured amount of drug (mg)}}{\text{Synthesized amount of delivery system (mg)}} \times 100$$

As shown in Table 3, it is confirmed to have stable physical and chemical properties in an aqueous solution phase. More specifically, it was confirmed that a solid lipid nanoparticle enclosing the poorly water-soluble drug (taxol) encapsulated the drug in 11% (w/w) efficiency, based on the weight of the solid lipid nanoparticle enclosing the poorly water-soluble drug (taxol), and had a size level of 80-100 nm and a surface charge level of 65-85 mV.

TABLE 3

| Size (nm) | Surface charge (mV) | Drug encapsulation efficiency (%) | Drug content (%, W/W) |
|---|---|---|---|
| 85.8.1 ± 1.6 | 71.3 ± 2.1 | 69 | 11 |

1-3: Preparation of Solid Lipid Nanoparticles Enclosing Poorly Water-soluble Drug (Taxol) Bound by Polymer Linker (PEG Derivative) (Taxol Containing SLN-PEG (Derivative)

The solid lipid nanoparticles enclosing the poorly water-soluble drug (taxol) prepared in above Example 1-1 has cationic amine ($-NH_2$) on the surface by DC-cholesterol. The cationic amine on the surface of solid lipid nanoparticle enclosing the poorly water-soluble drug (taxol) and a PEG derivative of above Chemical Formula 1 (n=106) (NOF Corporation) were reacted in a mole ratio of 1:3, with stirring at room temperature for one night, so that the solid lipid nanoparticle enclosing the poorly water-soluble drug (taxol) and the PEG derivative were chemically bonded by an amine-N-hydroxylsuccinimide (NHS) bond between cationic amine ($-NH_2$) of the solid lipid nanoparticle enclosing the poorly water-soluble drug (taxol) and N-hydroxysuccinimide (NHS) of the PEG derivative, and only solid lipid nanoparticles enclosing poorly water-soluble drug (taxol) bound by a polymer linker (PEG derivative) (Taxol containing SLN-PEG (derivative)) were separated through a Sephacryl S-200 column.

1-4: Preparation of Poorly Water-soluble Drug Delivery System Bound by Targeting Material (Cetuximab) (Taxol Containing SLN-PEG (Derivative)-cetuximab)

Traut's reagent dissolved in nitrogen-purged HEPES buffer (pH 8) as a solvent and cetuximab were stirred in a mole ratio of 1:1 at room temperature for 2 hours, and the amine group of cetuximab was substituted with a thiol group, and thereafter, only cetuximab wherein the amine group was substituted with a thiol group by a PD-10 column was purified and separated.

Cetuximab wherein the amine ($-NH_2$) group is substituted with a thiol ($-SH$) group was chemically bonded to the maleimide group (-maleimide) on the end of the PEG derivative bound to a solid lipid nanoparticle enclosing the poorly water-soluble drug (Taxol) bound by the polymer linker (PEG derivative) prepared in above Example 1-3 by a thiol-maleimide reaction at 4° C. for one night with stirring, and only the poorly water-soluble drug delivery system bound by the targeting material (cetuximab) (taxol containing SLN-PEG (derivative)-cetuximab) was separated through a Sephacryl S-200 column.

1-5: Physical and Chemical Properties of Poorly Water-soluble Drug Delivery System Bound by Targeting Material (Cetuximab)

The physical and chemical properties of the poorly water-soluble drug delivery system bound by the targeting material (cetuximab) prepared in Example 1-4 were measured in substantially the same manner as Example 1-2, and the results are described in Table 4.

As shown in Table 4, the physical and chemical properties of the poorly water-soluble drug delivery system bound by the targeting material (cetuximab) were confirmed, and specifically, it was confirmed that the poorly water-soluble drug delivery system bound by the targeting material (cetuximab) has a size level of 150-200 nm, and a surface charge level of −3 to 0 mV.

TABLE 4

| Size (nm) | Surface charge (mV) |
|---|---|
| 160.4 ± 0.9 | −1.3 ± 1.0 |

The poorly water-soluble drug delivery system bound by the targeting material (cetuximab) was observed by atomic force microscope. Specifically, the atomic force microscopic image was measured by dropping the poorly water-soluble drug delivery system bound by 100 µl of the targeting material (cetuximab) (5 mg/ml) on a transparent mica surface, and then removing the solvent by nitrogen drying, thereafter, chemically adsorbing only the poorly water-soluble drug delivery system bound by the targeting material (cetuximab) on the mica surface. A measurement condition was obtained using a XE-100 AFM system (Park System, Korea) in a non-contact mode having a scan area of 10 µm×10 µm, and the results are shown in FIG. 2.

Figure 1:
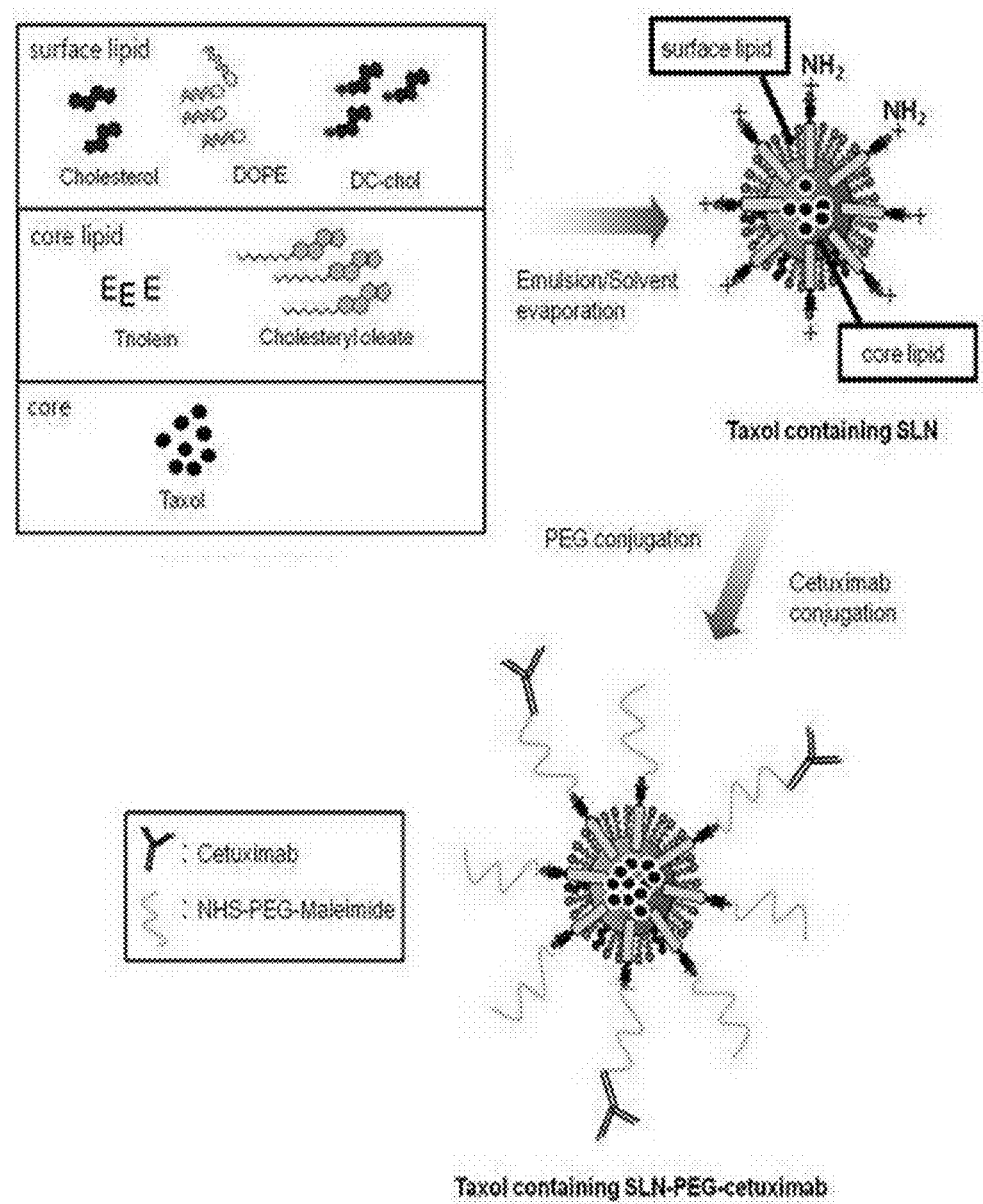
FIG. 1 is a schematic diagram representing synthesis process and constitution of a poorly water-soluble drug delivery system.
Figure 2:
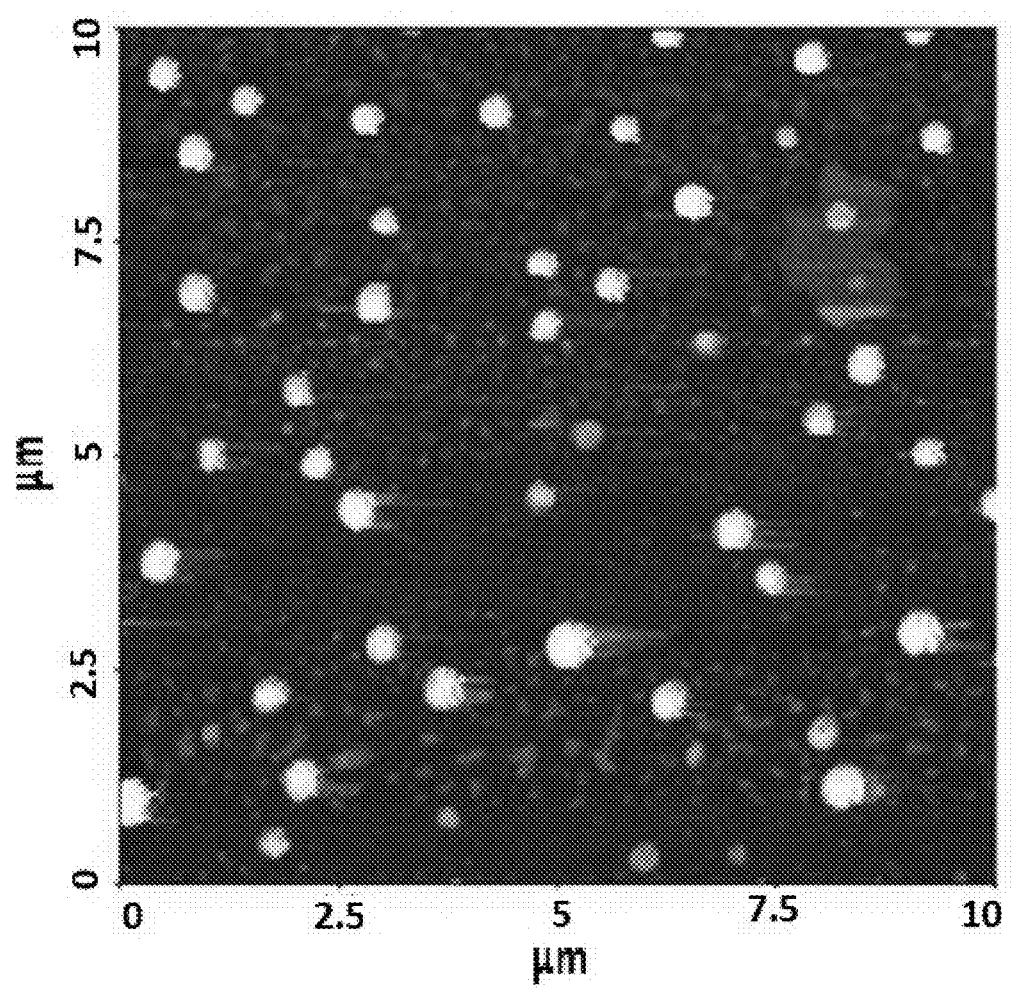
FIG. 2 is an atomic force microscopic image of a poorly water-soluble drug delivery system prepared in Example 1-4.

As shown in FIG. 2, it was confirmed with naked eyes that the poorly water-soluble drug delivery system bound by the targeting material (cetuximab) had a spherical shap, and had an uniform size with the deviation of the sizes being not big.

Example 2

Experiment of Anticancer Effect of Poorly Water-soluble Drug Delivery System in Lung Cancer Cell 2-1. Preparation of Poorly Water-soluble Drug Delivery System Bound by Targeting Material (Cetuximab) without Enclosing Drug (SLN-PEG (Derivative)-cetuximab (Vehicle))

As shown in following Table 5, nanoparticles were prepared in the same manner as Example 1-1, except that taxol was excluded from the components, and a drug delivery system without enclosing a drug (SLN-PEG (derivative)-cetuximab (vehicle)) was prepared in the same manner as Examples 1-3 and 1-4.

TABLE 5

| Classification | Components | Content (mg) | Content ratio (%) |
|---|---|---|---|
| Surface lipid part | DOPE | 5.2 | 19.7 |
| | Cholesterol | 1.8 | 6.8 |
| | DC-chol | 10.5 | 39.8 |
| Core lipid part | Cholesteryl oleate | 8.4 | 31.8 |
| | Triolein | 0.5 | 1.9 |

2-2. Preparation of Poorly Water-Soluble Drug Delivery System Bound by Targeting Material (Rituximab) (Taxol Containing SLN-PEG (Derivative)-rituximab)

A CD20+ cell targeting drug delivery system in which a targeting material of rituximab capable of targeting CD20+ is introduced on the surface of the nanoparticle was prepared in the same manner as above Example 1-4, except that rituximab was used as the targeting material.

2-3. Preparation of Lung Cancer Cell Line Derived Rodent

Lung cancer cell lines (NCI-H1975, ATCC CRL-5908) were diluted in 100 µl of matrigel by $1\times10^6$ each, and then was subcutaneously injected (s.c. injection) into 8-week-old mice (BALB/c-nu, Orient Bio Inc.) on right back (the part where the arms and legs of the mice may not reach), thereby leading a lung cancer cell line derived rodent lung cancer model. After 7 days, the size of the cancer was measured using a caliper, and when the size was about 50-100 mm$^3$, mice were divided into groups of 9 each so that the sizes of cancer are constant in each group, thereby preparing a lung cancer cell line derived rodent.

2-4. Check on Anticancer Effect in Lung Cancer Cell (NCI-H1975)

PBS, Taxol containing SLN prepared in Example 1-1, Taxol containing SLN-PEG (derivative) prepared in Example 1-3, Taxol containing SLN-PEG (derivative)-cetuximab prepared in Example 1-4, SLN-PEG (derivative)-cetuximab (vehicle) without a drug prepared in Example 2-1, and taxol containing SLN-PEG (derivative)-rituximab prepared in Example 2-2 were intravenously injected into cancer cell metastasized mice, and then the volume of the cancer tissue was measured (n=9).

Phosphate buffered saline (PBS) which is an isotonic solution having physically and chemically identical concentration to in vivo salt concentration, was administered to a mouse in the same volume as the other nanoparticle solution administered to a mouse intravenously, thereby being used as a control group corresponding to a mouse group not treated at all, and not expecting any effect. The taxol containing SLN-PEG (derivative) was used as a control for checking how effective cetuximab as the targeting material is as compared with taxol containing SLN-PEG (derivative)-cetuximab, and the taxol containing SLN was used as a control for checking how effective the derivative of polyethylene glycol (PEG) as a biocompatible polymer material for increasing in vivo retaining time as compared with taxol containing SLN-PEG (derivative)-cetuximab or Taxol containing SLN-PEG (derivative). Further, the taxol containing SLN-PEG (derivative)-rituximab has the same molecular weight and size (Mw 170,000) as compared with taxol containing SLN-PEG (derivative)-cetuximab, but is for checking the effect by a property capable of specifically targeting EGFR1 overexpressed in a lung cancer cell line (NCI-H1975) implanted in mice, and the rituximab used in the taxol containing SLN-PEG (derivative)-rituximab refers to a material having no specific reactivity to EGFR1.

Figure 3:
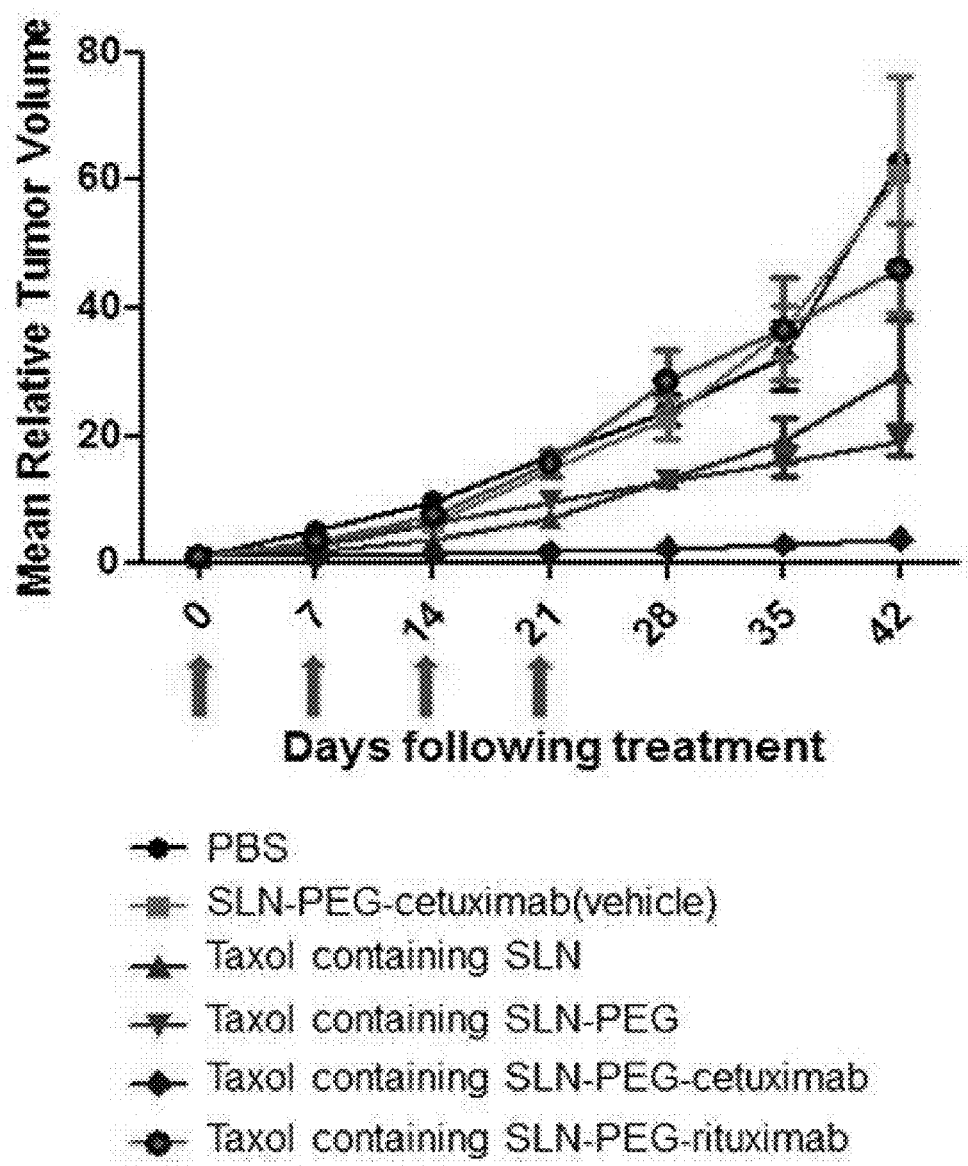
FIG. 3 is a graph of volumes of cancer tissues over time measured according to the method of Example 2-4, in order to check the therapeutic effect against cancer (lung cancer)

A sample was intravenously injected (i.v. injection) into a mouse prepared by above Example 2-3 in a content of 22 mg (taxol)/kg (dose of injected poorly water-soluble drug (taxol) per mass (kg) of a mouse) in each group once a week for 21 days, and the size of cancer was measured using a caliper once a week for total of 42 days including the period of administrating the sample, and calculated as following Equation 2, and the results are shown in FIG. 3.

Tumor Volume=½×larger diameter×(smaller diameter)$^2$ [Equation 2]

Larger diameter=a long axis of the cancer tissue, smaller diameter=a short axis of the cancer tissue As shown in FIG. 3, it was confirmed that the poorly water-soluble drug delivery system where cetuximab capable of targeting an EGFR1 antigen overexpressed in a lung cancer cell (H1975) as a targeting material is introduced into the surface (taxol containing SLN-PEG (derivative)-cetuximab), showed an excellent cancer treatment effect as compared with other controls.

Example 3

Experiment of Anticancer Effect of Poorly Water-Soluble Drug System in Breast Cancer Cell 3-1. Preparation of Poorly Water-soluble Drug Delivery System Bound by Targeting Material (Trastuzumab) (Taxol Containing SLN-PEG (Derivative)-herceptin)

A poorly water-soluble drug delivery system bound by a targeting material (trastuzumab) was prepared in the same manner as above Example 1-4, except that trastuzumab (trade name: Herceptin) was used as a targeting material.

3-2. Preparation of Breast Cancer Cell Line Derived Rodent

A breast cancer cell line derived rodent was prepared in the same manner as Example 2-3, except that a breast cancer cell (SK-BR-3, ATCC HTB-30) was used (n=6).

3-3. Check on Anticancer Effect in Breast Cancer (SK-BR-3)

PBS, taxol containing SLN-PEG (derivative) prepared in Example 1-3, and taxol containing SLN-PEG (derivative)-herceptin prepared in Example 3-1 were intravenously injected into cancer cell metastasized mice in the same manner as Example 2-4, and then the volume of the cancer tissue over time was measured, and the results are shown in FIG. 4 (n=6).

As shown in FIG. 4, it was confirmed that the poorly water-soluble drug delivery system bound by a targeting material (trastuzumab) where herceptin capable of targeting an EGFR2 which is an antigen overexpressed in a breast cancer cell (SK-BR-3) as a targeting material is introduced into the surface (taxol containing SLN-PEG (derivative)-herceptin), showed an excellent cancer treatment effect as compared with other controls.

Example 4

MTT Analysis 4-1. Preparation of Solid Lipid Nanoparticle without Encapsulation of Drug (SLN (Vehicle))

As shown in above Table 5, solid lipid nanoparticles without encapsulation of a drug were prepared in the same manner as above Example 1-1, except that taxol was excluded from the components.

4-2. Check on Cell Viability in Lung Cancer (NCI-H1975)

An anticancer efficacy was evaluated by measuring the cell viability using a method by a MTT reagent. NCI-H1975 cells were seeded in 96 wells to be $5\times10^3$ cells per well, and cultured for 24 hours, thereafter, SLN (vehicle) prepared in Example 4-1, taxol containing SLN prepared in Example 1-1, taxol containing SLN-PEG (derivative) prepared in Example 1-3, and taxol containing SLN-PEG (derivative)-cetuximab prepared in Example 1-4 were added to a well plate, respectively, and cultured in a $CO_2$ cell incubator at 37° C. for 72 hours. Thereafter, a medium (RPMI1640) was removed from the well plate, a MTT solution was added thereinto, the medium was cultured for further 4 hours, and then the MTT solution was removed. After a 0.04N hydrochloric acid-isopropanol solution was added, absorbance at 570 nm was measured using an elisa reader, and the results are shown in FIG. 5 (As a control, cells not treated at all were used).

As shown in FIG. 5, it was confirmed that a more enhanced cancer cell apoptosis effect appeared under a taxol containing SLN-PEG (derivative)-cetuximab condition. From these results, it was confirmed that taxol containing SLN-PEG (derivative)-cetuximab delivered taxol more effectively to the inside of a NCI-H1975 cell line, thereby representing a more enhanced anticancer efficacy.

4-3. Check on Cell Viability in Breast Cancer (SK-BR-3)

The same method as above Example 4-2 was used, except that taxol containing SLN-PEG(derivative)-herceptin was used instead of taxol containing SLN-PEG(derivative)-cetuximab, and the results are shown in FIG. 6 (As a control, cells not treated at all were used).

As shown in FIG. 6, it was confirmed that a more enhanced cancer cell apoptosis effect appeared under a taxol containing SLN-PEG (derivative)-herceptin condition. From these results, it was confirmed that taxol containing SLN-PEG (derivative)-herceptin delivered taxol more effectively to the inside of a SK-BR-3 cell line, thereby representing a more enhanced anticancer efficacy.

Example 5

FACS Analysis 5-1. Preparation of Wight 488 Conjugated Taxol Containing SLN

Cationic amine ($-NH_2$) of the solid lipid nanoparticle enclosing a drug (taxol) prepared in above Example 1-1 and Dylight 488 NHS ester (Mw 1011) (Thermoscientific) were reacted in a mole ratio of 10:1 mol/mol, with stirring at room temperature at one night, thereby chemically bonding the solid lipid nanoparticle enclosing the drug (taxol) and a fluorescent material (Dylight 488 NHS ester) by an amine-N-hydroxysuccinimide (NHS) bond between cationic amine ($-NH_2$) of the solid lipid nanoparticle enclosing the drug (taxol) and Dylight 488 NHS ester, and only Dylight 488 conjugated taxol containing SLN, bound by only fluorescent material was separated through a Sephacryl S-200 column.

5-2. Preparation of Dylight 488 Conjugated Taxol Containing SLN-PEG (Derivative)

Dylight 488 conjugated taxol containing SLN-PEG (derivative) was prepared in the same manner as above Example 1-3 using Dylight 488 conjugated taxol containing SLN prepared in above Example 5-1.

5-3. Preparation of Dylight 488 Conjugated Taxol Containing SLN-PEG (Derivative)-cetuximab Dylight 488 conjugated taxol containing SLN-PEG (derivative)-cetuximab was prepared in the same manner as above Example 1-4 using Dylight 488 conjugated taxol containing SLN-PEG (derivative) prepared in above Example 5-2.

5-4. Preparation of Dylight 488 Conjugated Taxol Containing SLN-PEG (Derivative)-herceptin Dylight 488 conjugated taxol containing SLN-PEG(derivative)-herceptin was prepared in the same manner as above Example 1-4, except that herceptin was used instead of cetuximab, and using Dylight 488 conjugated taxol containing SLN-PEG (derivative) prepared in above Example 5-2.

5-5. Delivery Efficiency Evaluation in NCI-H1975 Cell Line

NCI-H1975 cells were seeded in 6 wells to be $2\times10^4$ cells per well, and cultured for 24 hours, thereafter, Dylight 488 conjugated taxol containing SLN prepared in Example 5-1, Dylight 488 conjugated taxol containing SLN-PEG (derivative) prepared in Example 5-2, Dylight 488 conjugated taxol containing SLN-PEG (derivative)-cetuximab prepared in Example 5-3 were added to a well plate, respectively, and cultured in a $CO_2$ cell incubator at 37° C. for 0.5 hours. Thereafter, a medium (RPMI1640) was removed from a well plate, and then TrypLE™ Express was added to detach cells adhered to the well plate, and the medium was redispersed in phosphate buffered saline (PBS), then BD FACS CALIBUR as a fluorescence flow cytometry was used to perform measurement. The results are shown in FIG. 7 (As a control, cells not treated at all were used).

As shown in FIG. 7, a better cell fluorescence intensity peak shift was confirmed under a Dylight 488 conjugated taxol containing SLN-PEG (derivative)-cetuximab condition. From these results, it was confirmed that taxol containing SLN-PEG (derivative)-cetuximab delivered a poorly water-soluble drug (taxol) more effectively to the inside of a NCI-H1975 cell line, thereby representing a more enhanced delivery efficiency.

5-6. Delivery Efficiency Evaluation in SK-BR-3 Cell Lines

Measurement was performed in the same manner as Example 5-5, except that Dylight 488 conjugated taxol containing SLN-PEG (derivative)-herceptin was used instead of Dylight 488 conjugated taxol containing SLN-PEG (derivative)-cetuximab, and SK-BR-3 cells were used instead of NCI-H1975 cells, and the results are shown in FIG. 8 (As a control, cells not treated at all were used).

As shown in FIG. 8, a better cell fluorescence intensity peak shift was confirmed under a Dylight 488 conjugated taxol containing SLN-PEG (derivative)-herceptin condition. From these results, it was confirmed that taxol containing SLN-PEG (derivative)-herceptin delivered a poorly water-soluble drug (taxol) more effectively to the inside of a SK-BR-3 cell line, thereby representing a more enhanced delivery efficiency.

Example 6

Anticancer Efficacy of Taxol-Containing SLN-PEG-cetuximab

In order to verify excellent anticancer effect of the poorly water-soluble drug delivery system enclosing taxol therein, an anticancer effect of injected taxol containing SLN-PEG-cetuximab depending on the concentration was observed. This is for checking the concentration range of the injectable poorly water-soluble drug delivery system from which the anticancer effect is observed, by observing the anticancer effect depending on the concentration of the injected poorly water-soluble drug delivery system.

A lung cancer cell line derived rodent was prepared in the same manner as above Example 2-3, except that when the size became 50~100 mm$^3$, mice were divided into groups of 4 each so that the sizes of cancer are constant in each group.

Maximum tolerance dose (MTD; a dose at which about 10% of weight loss is observed, a dose at which severe toxicological change is not observed, and a maximum amount at which death is not observed) were checked through an experiment. Doses of 0, 100, 200, 400 mg (nanoparticles enclosing a poorly water-soluble drug)/kg (mouse) were intravenously injected to each mouse group, respectively by dose, and thereafter, were intravenously injected again, after 1, 2, 3 and 4 days (total four injections), and the weight change and state of the mice during injection period (movement, dead or alive) were observed. In the administered dose, 0 means PBS solution (phosphate buffered saline, pH7.4), and as a result of an experiment, 200 mg (nanoparticles enclosing a poorly water-soluble drug)/kg (mouse) or 22 mg (taxol)/kg (mouse) was established as a MTD value of Taxol containing SLN-PEG (derivative)-cetuximab.

PBS (a group from which no effect is expected), doses of 1.1, 2.2, 5.5, 11 and 22 mg (taxol)/kg (mouse) were intravenously injected into each mouse group for dose, respectively, and thereafter, intravenously injected again after 7, 14 and 21 days (total 4 injections), and the results are shown in FIG. 9.

As shown in FIG. 9, volume change of a cancer tissue over time for each group was checked. In order to analyze the result, the significant difference in cancer tissue volume on day 21, between a group to which a MTD value of 22 mg (taxol)/kg (mouse) was injected, and another groups (11, 5.5, 2.2 and 1.1 mg (taxol)/kg (mouse) injected group), was evaluated, using a student's t-test statistical method. More specifically, when analyzed using a student's t-test statistical method, p-value of 0.01 or less means that the group has a significant difference in cancer tissue volume from the group to which a MTD value of 22 mg (taxol)/kg (mouse) was injected, and p-value of 0.01 or more means that the group has no significant difference in cancer tissue volume from the group to which a MTD value of 22 mg (taxol)/kg (mouse).

When evaluating the significant difference in cancer tissue volume on day 21 between a group to which a MTD value of 22 mg (taxol)/kg (mouse) was injected and the remaining group (11, 5.5, 2.2 and 1.1 mg (taxol)/kg (mouse) injected group), p-value of 1.1 mg (taxol)/kg (mouse) injected group was represented to be 0.01 or less. This means that the group has a significant difference in cancer tissue volume from the group to which MTD value of 22 mg (taxol)/kg (mouse) was injected.

The p-values of the remaining groups (11, 5.5 and 2.2 mg (taxol)/kg (mouse) injected groups) were represented to be 0.01 or more. This means that the groups have no significant difference in cancer tissue volume from the group to which MTD value of 22 mg (taxol)/kg (mouse) was injected, and it can be seen therefrom that even in the case of injecting 11, 5.5 and 2.2 mg (taxol)/kg (mouse), the same anticancer effect as the case of injecting the MTD value of 22 mg (taxol)/kg (mouse), is generated.

Therefore, it was recognized that the injectable concentration at which a maximum anticancer effect of the poorly water-soluble drug delivery system is observed is 2.2-22 mg (taxol)/kg (mouse).

Example 7

Comparison Experiment with Genexol®-PM

Genexol®-PM (Samyang corporation) having a micelle structure which is nanoparticles enclosing taxol therein currently being used for anticancer treatment of cancer patients was chosen as a control, and compared for the cancer treatment effect.

A lung cancer cell line derived rodent was prepared in the same manner as above Example 2-3, except that when the size became 50~100 mm3, mice were divided into groups of 6 each so that the sizes of cancer are constant in each group.

As doses intravenously administered to the mice, Genexol®-PM and Taxol containing SLN-PEG (derivative)-cetuximab were administered in a MTD value, respectively.

Regarding the MTD value of Genexol®-PM, a paper of Samyang incorporation which is the manufacture of Genexol®-PM, was referenced (In vivo evaluation of polymeric micellar paclitaxel formulation: toxicity and efficacy. Journal of Controlled Release 2012; 72:191-202).

When intravenously administering, the experiment was carried out in the same manner as above Example 2-4, except that the amount of taxol containing SLN-PEG (derivative)-cetuximab prepared in above Example 1-4 was 22 mg (taxol/kg (mouse), and the amount of Genexol®-PM was 60 mg (taxol)/kg (mouse), and the results are shown in FIG. 10.

As shown in FIG. 10, it was confirmed that taxol containing SLN-PEG (derivative)-cetuximab had better anticancer effect than Genexol®-PM.

As shown in following Table 6, the content range of taxol substantially injected into a body of taxol containing SLN-PEG (derivative)-cetuximab was 22 mg (taxol)/kg (mouse). However, like the results of Example 6, the MTD value of 22 mg (taxol)/kg (mouse) had no statistically significant difference from administration of 2.2 mg (taxol)/kg (mouse), and this includes less content than 60 mg (taxol)/kg (mouse) which is the content of taxol injected by Genexol®-PM, and thus, taxol containing SLN-PEG (derivative)-cetuximab is expected to show a better anticancer effect than currently commercially available Genexol®-PM with a less taxol content. Further, since taxol containing SLN-PEG (derivative)-cetuximab may represent a better anticancer effect with a less taxol content, if the concentration of the injected poorly water-soluble drug delivery system is controlled to adjust the content of taxol, the side effect due to taxol may be minimized, while a better anticancer effect may be represented. These results are due to an excellent targeting ability and a poorly water-soluble drug delivery ability of the poorly water-soluble drug delivery system to a cancer tissue.

TABLE 6

|  | Taxol containing SLN-PEG-cetuximab | Genexol ®-PM |
|---|---|---|
| Maximum tolerance dose (MTD) (mg (taxol)/kg (mouse)) | 22 | 60 |
| Injection concentration range representing anticancer effect (mg (taxol)/kg (mouse)) | 2.2~22 | n/a |

The invention claimed is:
1. A targeting poorly water-soluble drug delivery system comprising:
a solid nanoparticle comprising a core lipid part containing cholesteryl ester and triglyceride, and a surface lipid part containing phospholipid, cholesterol and cationic lipid,
a poorly water-soluble drug encapsulated in the solid nanoparticle, and
a targeting material connected to the surface lipid part by a polymer linker,
wherein the polymer linker is represented by chemical formula 1:

Chemical formula 1

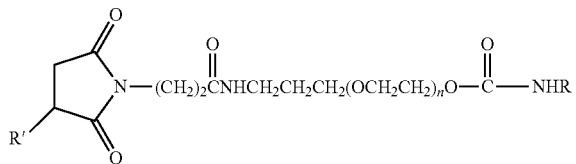

where R is the cationic lipid of the surface lipid part;
where R' is the targeting material;
where n is an integer of 4 to 1130; and
where the drug delivery system improves apoptosis efficiency relative to a solid nanoparticle comprising the poorly water-soluble drug alone.

2. The drug delivery system of a poorly water-soluble drug according to claim 1, wherein the drug delivery system comprises 30 to 60 wt % of cholesteryl ester; 0.1 to 10 wt % of triglyceride; 5 to 30 wt % of phospholipid; 5 to 20 wt % of cholesterol; cationic lipid 10 to 50 wt % of; and 10 to 20 wt % of the poorly water-soluble drug.

3. The drug delivery system of a poorly water-soluble drug according to claim 1, wherein the cholesteryl ester is an ester compound of an unsaturated fatty acid having a carbon number of 10 to 24, and cholesterol.

4. The drug delivery system of a poorly water-soluble drug according to claim 1, wherein the triglyceride is at least one selected from the group consisting of triacetin, tributyrin, tricaproin, tricaprylin, tricaprin and triolein.

5. The drug delivery system of a poorly water-soluble drug according to claim 1, wherein the phospholipid is at least one selected from the group consisting of dioleoylphosphatidylethanolamine (DOPE), palmitoyloleoylphosphatidylcholine (POPC), egg phosphatidylcholine (EPC), distearoylphosphatidylcholine (DSPC), dioleoylphosphatidylcholine (DOPC), dipalmitoylphosphatidylcholine (DPPC), dioleoylphosphatidylglycerol (DOPG) and dipalmitoylphosphatidylglycerol (DPPG).

6. The drug delivery system of a poorly water-soluble drug according to claim 1, wherein the cationic lipid is at least one selected from the group consisting of 3beta-[N—(N',N',N'-trimethylaminoethan)carbamoyl]cholesterol (TC-cholesterol), 3beta[N—(N',N'-dimethylaminoethane)carbamoyl]cholesterol (DC-cholesterol), 3beta[N—(N'-monomethylaminoethane)carbamoyl]cholesterol (MC-cholesterol), 3beta[N-(aminoethane)carbamoyl]cholesterol (AC-cholesterol), N—(N'-aminoethane)carbamoylpropanoictocoperol (AC-tocoperol), N—(N'-methylaminoethane) carbamoylpropanoictocoperol (MC-tocoperol), N,N-dioleyl-N,N-dimethylammonium chloride(DODAC), N,N-disterayl-N,N-dimethylammonium bromide (DDAB), N-(1-(2,3-dioleoyloxy)propyl-N,N,N-trimethylammonium chloride (DOTAP), N,N-dimethyl-(2,3-dioleoyloxy)propylamine (DODMA), N-(1-(2,3-dioleoyloxy)propyl)-N,N,N-trimethylammonium chloride (DOTMA), 1,2-dioleoyl-3-dimethylammonium-propane (DODAP), 1,2-dioleoylcarbamyl-3-dimethylammonium-propane (DOCDAP), 1,2-dilinoyl-3-dimethylammonium-propane (DLINDAP), dioleoyloxy-N-[2-sperminecarboxamido)ethyl}-N,N-dimethyl-1-propane aminium trifluoro-acetate (DOSPA), dioctadecyl-amidoglycylspermine (DOGS), 1,2-dimyristyloxypropyl-3-dimethyl-hydroxyethylammonium-bromide (DMRIE), 3-dimethylamino-2-(chlest-5-en-3-beta-oxybutane-4-oxy)-1-(cis,cis-9, 12-oc- tadicadienoxy) propane (CLinDMA), 2-[5'-(cholest-5-ene-3beta-oxy)-3'-oxapentoxy)-3-dimethyl-1-(cis,cis-9', 1-2'-octadicardienoxy)propane (CpLinDMA), N,N-dimethyl-3,4-dioleoyloxybenzylamine (DMOBA), 1,2-N,N'-dioleylcarbamyl-3-dimethylaminopropane (DOcarbDAP), 1,2-diacyl-3-trimethylammonium-propane (TAP) and 1,2-diacyl-3-dimethylammonium-propane (DAP).

7. The drug delivery system of a poorly water-soluble drug according to claim 1, wherein the targeting material is at least one selected from the group consisting of bevacizumab, erlotinib, gefitinib, imatinib mesylate, cetuximab, rituximab, trastzumab, folate and RGD.

8. The drug delivery system of a poorly water-soluble drug according to claim 1, wherein the poorly water-soluble drug is at least one selected from the group consisting of poorly water-soluble anticancer agent, antiviral agent, steroidal anti-inflammatory drug, antibiotic, antifungal agent, vitamin, prostacyclin, anti-metabolic agent, mitotic, adrenaline antagonist, antiepileptic drug, anti-anxiety drug, tranquilizer, antidepressant, anesthetic drug, pain killer, anabolic steroid, immunosuppressive agent, and immune-stimulant.

9. The drug delivery system of a poorly water-soluble drug according to claim 1, wherein the poorly water-soluble anticancer agent is at least one selected from the group consisting of taxol, idarubicin, mitoxantrone, paclitaxel, docetaxel, methotrexate, trimetrexate, thioguanine, mercaptopurine, cladrabine, amrubicin, octreotide, gosereline, leuprolide, flutamide, casodex, doxorubicin, 5-fluorouracil, fludarabine, cytarabine, mitomycin-C, styrene maleic acid neocarzinostatin (SMANCS), cisplatin, carboplatin, oxaliplatin, carmustine (BCNU), dacabazine, etoposide, daunomycin, dactinomycin, vinca alkaloid, bleomycin, cyclophosphamide, ifosamide, gemcitabine, pemetrexed, camptothecin, irinotecan, topotecan, chlorambucil and melphalan.

10. The drug delivery system of a poorly water-soluble drug according to claim 1, wherein the particle size of the drug delivery system ranges from 30 to 300 nm.

11. The drug delivery system of a poorly water-soluble drug delivery system of a poorly water-soluble drug according to claim 1 at an amount of 20 to 200 mg/kg.

12. A method of preparing the drug delivery system of poorly water-insoluble drug according to claim 1, comprising dissolving cholesteryl ester, triglyceride, phospholipid, cholesterol, cationic lipid and poorly water-soluble drug in an organic solvent and adding water to prepare a solid nanoparticle which comprises a core lipid part comprising cholesteryl ester and triglyceride and a surface lipid part comprising phospholipid, cholesterol and cationic lipid; a poorly water-soluble drug encapsulated in the core lipid part; binding a polymeric linker to the surface lipid part of nanoparticle through amide bond, and attaching a targeting material to the polymeric linker.

13. The method according to claim 12, wherein boiling point of the organic solvent is lower than melting point of cholesterol ester and lower than boiling point of water.

* * * * *